US007184812B2

(12) United States Patent
Sinderby et al.

(10) Patent No.: US 7,184,812 B2
(45) Date of Patent: Feb. 27, 2007

(54) CONTROL OF INTER-ELECTRODE RESISTIVITY TO IMPROVE QUALITY OF MEASURED ELECTRICAL BIOLOGICAL SIGNALS

(75) Inventors: Christer Sinderby, Toronto (CA); Lars Lindstrom, Molndal (SE)

(73) Assignee: Maquet Critical Care AB, Solna (SE)

( * ) Notice: Subject to any disclaimer, the term of this patent is extended or adjusted under 35 U.S.C. 154(b) by 296 days.

(21) Appl. No.: 10/726,750

(22) Filed: Dec. 2, 2003

(65) Prior Publication Data
US 2004/0230110 A1 Nov. 18, 2004

Related U.S. Application Data

(60) Provisional application No. 60/470,339, filed on May 13, 2003.

(51) Int. Cl.
*A61B 5/04* (2006.01)
(52) U.S. Cl. .............. 600/393; 600/380; 600/546; 600/547
(58) Field of Classification Search ............ 600/380, 600/393, 546, 547
See application file for complete search history.

(56) References Cited

U.S. PATENT DOCUMENTS

| | | | |
|---|---|---|---|
| 4,078,553 A * | 3/1978 | Duroux | 600/384 |
| 4,465,074 A * | 8/1984 | Buchalter | 600/397 |
| 5,024,228 A | 6/1991 | Goldstone et al. | |
| 5,125,406 A | 6/1992 | Goldstone et al. | |
| 5,257,635 A | 11/1993 | Langberg | |
| 5,327,888 A | 7/1994 | Imran | |
| 5,341,806 A | 8/1994 | Gadsby et al. | |
| 5,671,752 A | 9/1997 | Sinderby et al. | |
| 5,772,591 A | 6/1998 | Cram | |
| 5,820,560 A | 10/1998 | Sinderby et al. | |
| 5,991,650 A * | 11/1999 | Swanson et al. | 600/374 |
| 6,134,480 A * | 10/2000 | Minogue | 607/152 |
| 6,148,222 A * | 11/2000 | Ramsey, III | 600/380 |

(Continued)

FOREIGN PATENT DOCUMENTS

WO    WO 01/64102    *  7/2001

OTHER PUBLICATIONS

Daubenspeck et al., "Diaphragmatic electromyography using a multiple electrode array," J Appl Physiol., Oct. 1989, No. 67(4), pp. 1525-1534.

(Continued)

*Primary Examiner*—Lee S. Cohen
(74) *Attorney, Agent, or Firm*—Fay Kaplun & Marcin, LLP

(57) ABSTRACT

Described is an electrode array for measuring electrical activity in a subject's biological tissue, comprising an electrode support, a group of electrodes mounted on the electrode support, and an inter-electrode conductive medium having a given resistivity for controlling resistivity between the electrodes of the group. Also, described is a method for controlling the inter-electrode resistivity in the electrode array comprises providing the inter-electrode conductive medium having the given resistivity between the electrodes of the group, and interconnecting the electrodes of the group through this inter-electrode conductive medium to control resistivity between the electrodes. In this manner, when contact between at least one electrode of the group and the subject's biological tissue is poor, an estimate of the electrical activity in the subject's biological tissue is produced on this electrode through the inter-electrode conductive medium, this estimate being a mean value of electrical potentials produced on neighbouring electrodes of the group by the electrical activity in the subject's biological tissue.

30 Claims, 3 Drawing Sheets

U.S. PATENT DOCUMENTS

| | | |
|---|---|---|
| 6,233,472 B1 | 5/2001 | Bennet et al. |
| 6,259,938 B1 | 7/2001 | Zarychta et al. |
| 6,357,447 B1 | 3/2002 | Swanson et al. |
| 6,434,421 B1 | 8/2002 | Taheri |
| 6,438,400 B1 | 8/2002 | Beard et al. |
| 6,584,347 B1 | 6/2003 | Sinderby |

OTHER PUBLICATIONS

Luo et al., "Diaphragm EMG measured by cervical magnetic and electrical phrenic nerve stimulation," J Appl Physiol, Dec. 1998, No. 85(6), pp. 2089-2099.

Viale et al., "Time course evolution of ventilatory responses to inspiratory unloading in patient," Am J Respir Crit Care Med., No. 157, pp. 428-434, 1998.

Becket al., "Effects of muscle-to-electrode distance on the human diaphragm electromyogram," J Appl Physiol, 1995, No. 79, pp. 975-985.

Becket. al., "Influence of bipolar esophageal electrode positioning on measurements of human crural diaphragm," EMG. J Appl Physiol, No. 81, pp. 1434-1449.

* cited by examiner

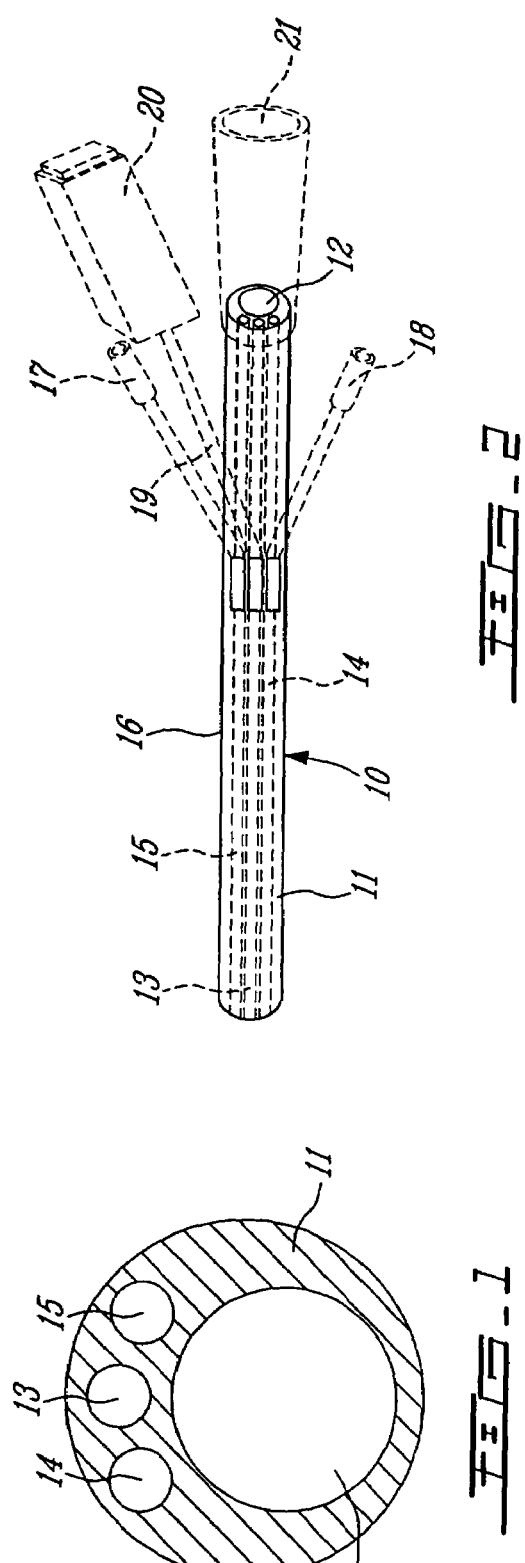
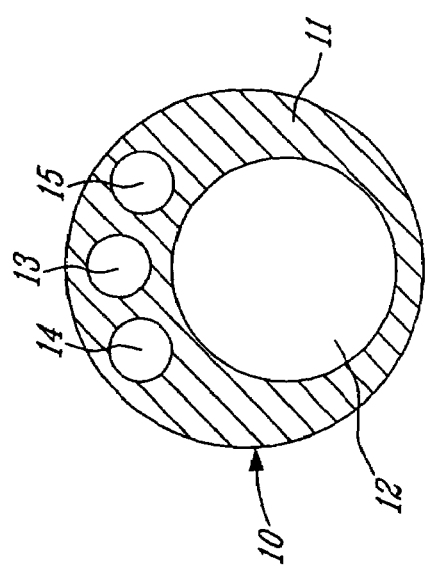
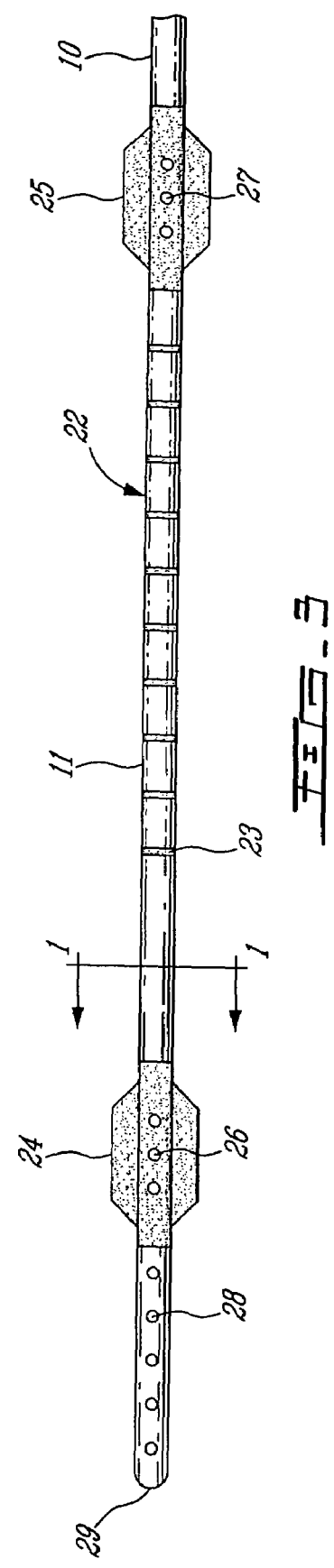

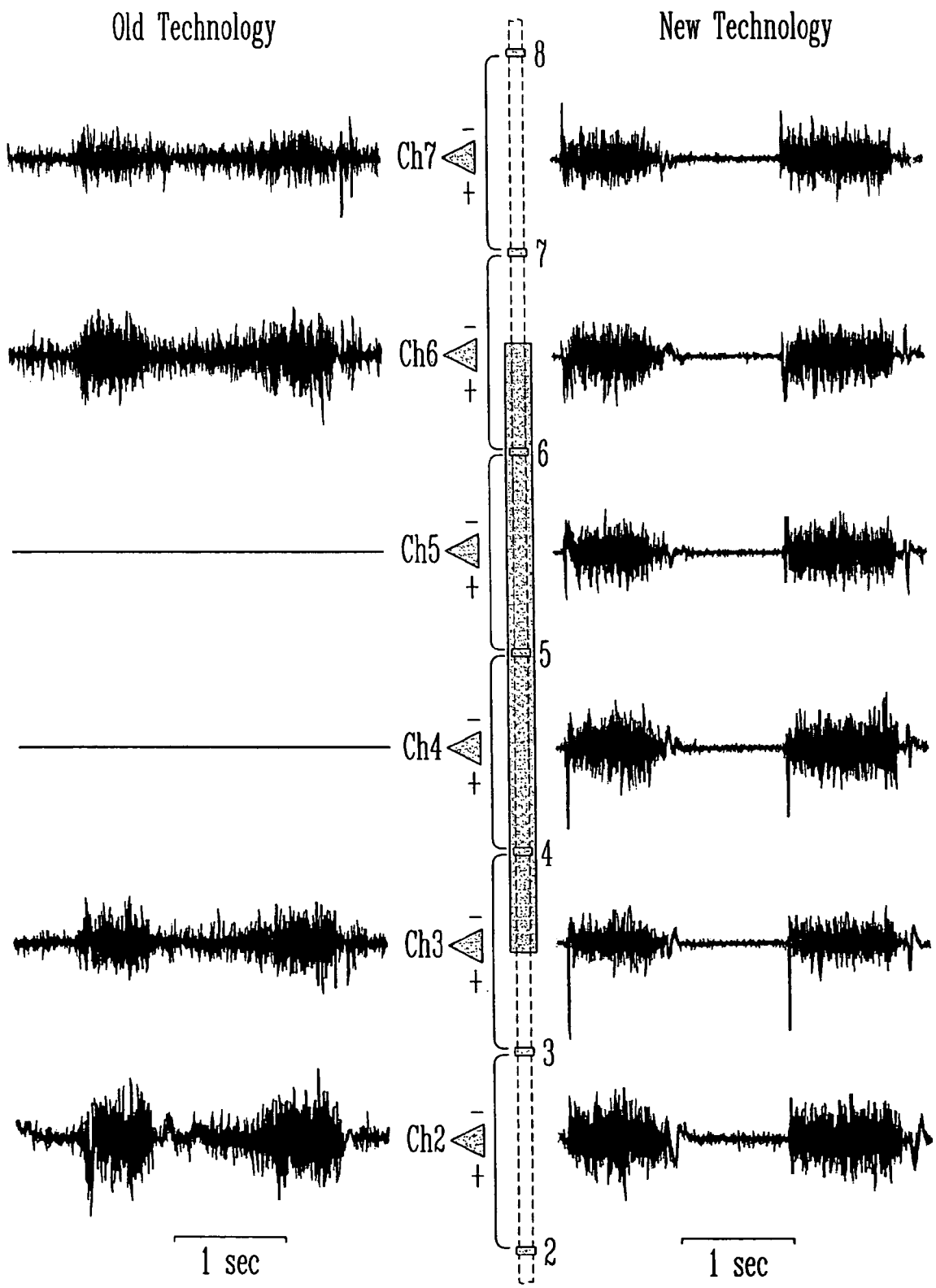
FIG_5

CONTROL OF INTER-ELECTRODE RESISTIVITY TO IMPROVE QUALITY OF MEASURED ELECTRICAL BIOLOGICAL SIGNALS

PRIORITY CLAIM

This Application claims the benefit of the U.S. Provisional Application Ser. No. 60/470,339 filed on May 13, 2003 which is expressly incorporated herein, by reference.

FIELD OF THE INVENTION

The present invention relates to a method for controlling inter-electrode resistivity and to an electrode array having an inter-electrode resistivity controlled by this method.

BACKGROUND OF THE INVENTION

The current technology uses electrodes to measure electrical activity in a subject's biological tissue, e.g. muscles. Each electrode is either bare or individually covered with a conductive medium while the highest possible resistivity is maintained between the electrodes.

The use of an electrode array to measure electrical signals from, for example, a muscle requires that at least one signal electrode and a reference electrode be in contact with the subject's biological tissue via an electrically conducting medium to produce a defined muscle-related electric potential. If an electrode is in a poor electrically conducting medium, e.g. loses contact with the biological tissue and is isolated in air, it will deliver a non defined electric potential dominated by capacitive disturbances; the electrode will then act similar to an antenna. An electrically conducting medium can comprise any electrolyte or conductive substance/material. Such a non defined electric potential can still present an amplitude higher than the common noise level and can be mistakenly included in the signal processing as a valid signal representative of the electrical activity of the subject's muscle.

A poor electrically conducting medium or the absence of electrically conducting medium between one electrode of an array and the subject's biological tissue will cause a loss of the balancing "half-cell potential" and change the electrode potential relative to the electric potentials on the other electrodes of the array that have maintained contact with the biological tissue; more specifically, the DC potential will be altered. Also, the loss of contact of one electrode with the biological tissue increases the electrode impedance and also makes the electrode more sensitive to capacitively-induced disturbances. Consequently, the electric potentials on the various electrodes of the array will be different depending on whether these electrodes maintain or not contact with the subject's biological tissue. Accurate measurements require either removal of the DC component or removal of the channels with DC offset. Offset problems affect primarily the first amplification stage, which has to produce limited gain in case of large DC levels.

Recently, the feasibility of improving signal quality by covering an electrode array for measuring electrical activity in a subject's biological tissue with a mesh/matrix was demonstrated.

However, no method/technology is known or currently used to control the inter-electrode resistivity of an electrode array for the purpose of improving quality of the measured signals related to electrical activity of a subject's biological tissue. Control of the inter-electrode resistivity of an electrode array results in improvement of the signal quality by eliminating artifactual influences/disturbances due to poor electrode-to-tissue contact.

SUMMARY OF THE INVENTION

According to the invention, there is provided a method of controlling an inter-electrode resistivity in an electrode array including a group of electrodes for measuring electrical activity in a subject's biological tissue, comprising providing an inter-electrode conductive medium having a given resistivity between the electrodes of the group, and interconnecting the electrodes of the group through this inter-electrode conductive medium to thereby control resistivity between the electrodes.

The present invention also relates to an electrode array for measuring electrical activity in a subject's biological tissue, comprising:

an electrode support;
a group of electrodes mounted on the electrode support; and
an inter-electrode conductive medium having a given resistivity for controlling resistivity between the electrodes of the group.

Further in accordance with the present invention, there is provided an electrode array for measuring electrical activity in a subject's biological tissue, comprising:

a catheter with a distal end section;
a series of electrodes mounted on the distal end section of the catheter; and
an inter-electrode conductive medium having a given resistivity for controlling resistivity between the electrodes of the series.

In this manner, when contact between at least one electrode of the group and the subject's biological tissue is poor, an estimate of the electrical activity in the subject's biological tissue is produced on this electrode through the inter-electrode conductive medium. This estimate is constituted by a mean value of electrical potentials produced on neighbouring electrodes of the group by the electrical activity in the subject's biological tissue.

According to a non-restrictive illustrative embodiment, the inter-electrode conductive medium between the electrodes may include a reference electrode.

The foregoing and other objects, advantages and features of the present invention will become more apparent upon reading of the following non-restrictive description of an illustrative embodiment thereof, given by way of example only with reference to the accompanying drawings.

BRIEF DESCRIPTION OF THE DRAWINGS

In the appended drawings:

FIG. 1 is a cross sectional view of a catheter forming part of an illustrative embodiment of the electrode array according to the present invention, this cross sectional view being taken along line 1—1 of FIG. 3;

FIG. 2 is a side elevational view of a proximal end section of the catheter of FIG. 1;

FIG. 3 is a side elevational view of a distal, free end section of the catheter of FIGS. 1 and 2, on which a series of electrodes are mounted;

FIG. 5 is a graph depicting signals obtained from an electrode array using a reference amplifier and digital differentiation for, on the left side, the previous technology and, on the right side, the technology according to the present invention.

DETAILED DESCRIPTION OF THE ILLUSTRATIVE EMBODIMENT

Figure 4:
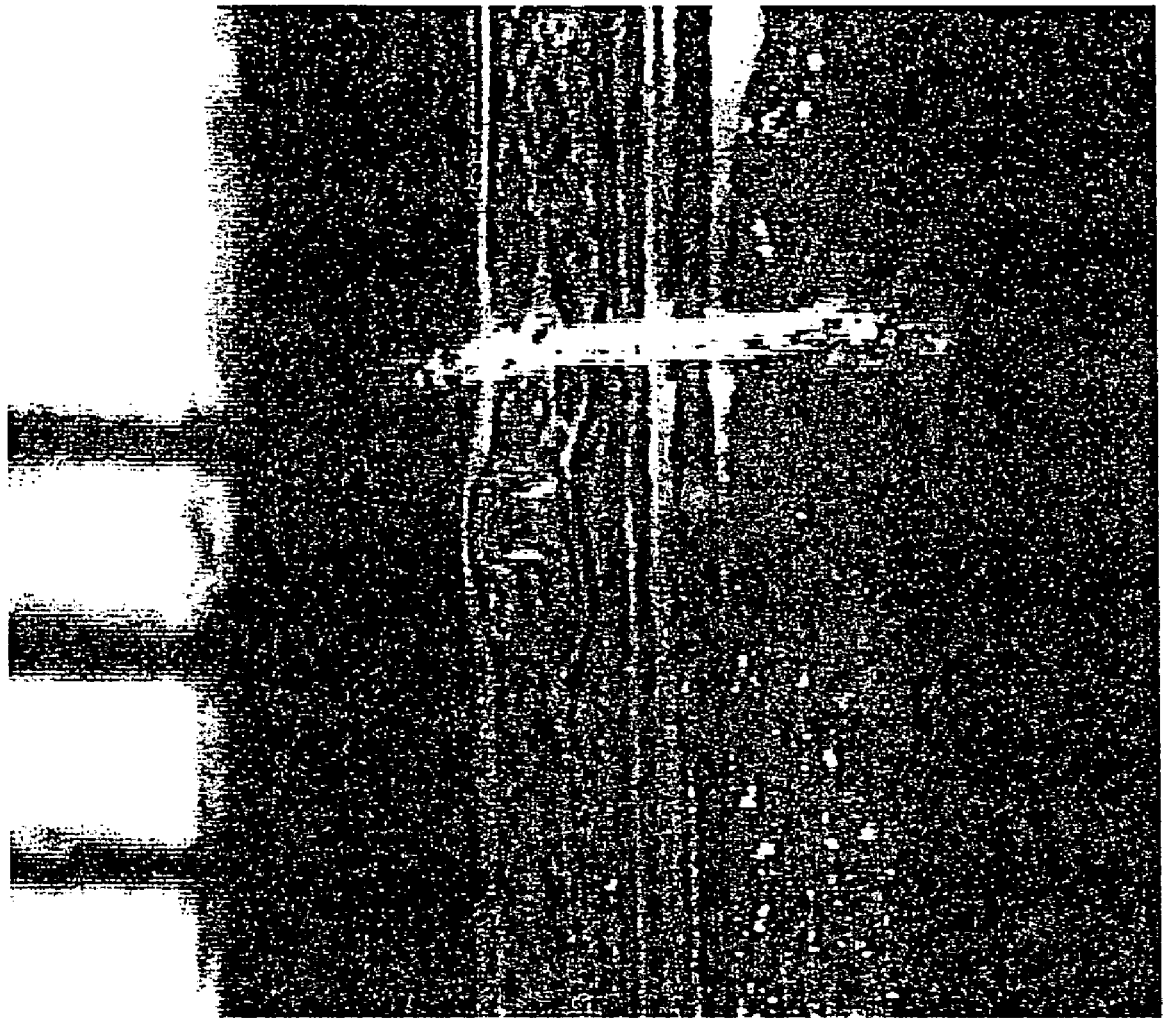
FIG. 4 is a photograph showing an electrode of the illustrative embodiment of the electrode array according to the present invention, embedded within an inter-electrode conductive medium.

The non-restrictive illustrative embodiment of the electrode array according to the present invention will now be described with reference to the accompanying drawings.

The non-restrictive illustrative embodiment of the present invention will be described in relation to an application of the electrode array to the detection of electromyographic (EMG) activity of a subject's diaphragm. Therefore, in this illustrative embodiment, the biological tissue is the subject's tissue nearby the diaphragm. However, it should be kept in mind that the present invention is not limited to this particular application and can be used as well for detecting other types of electrical activity, electromyographic or not, of a subject's body.

Structure of the Illustrative Embodiment of the Electrode Array

The illustrative embodiment of the electrode array comprises, as electrode support, an esophageal catheter 10 (FIGS. 1–3). The esophageal catheter 10 will enable insertion of the electrode array through the subject's esophagus and positioning of the electrodes in the vicinity of the subject's diaphragm.

As illustrated in the cross sectional view of FIG. 1, the esophageal catheter 10 comprises a tube 11 made of polyurethane (Tecoflex™) including four (4) longitudinal lumens 12–15. The lumens of the polyurethane tube 11 comprises:

a larger-diameter lumen 12 used for feeding the subject (eventually an extra lumen can be added for venting gas);
a smaller-diameter lumen 13 through which electrical wires run; and
two (2) smaller-diameter pressure lumens 14 and 15 used for supplying or venting gas under pressure.

FIG. 2 illustrates a proximal end section 16 of the esophageal catheter 10. As illustrated in FIG. 2, the pressure lumen 15 is teed off to a gastric pressure connector 17 while the pressure lumen 14 is teed off to an esophageal pressure connector 18. The electrical wires 19 running through the lumen 13 are teed off (electrically connected) to an electrical connector 20 for connection to signal-processing equipments. Finally, a feeding connector 21 is connected to the larger-diameter lumen 12.

FIG. 3 illustrates the distal, free end section 22 of the catheter 10.

Isolation of a free end section of the wires 19 running through the lumen 13 is removed. The non-isolated free end section of each wire 19 is passed through a small hole extending from the inner face of the lumen 13 to the outer face of the polyurethane tube 11 (outer face of the catheter 10) to expose this non-isolated free end section of the wire 19 outside the catheter 10. The exposed non-isolated free end section of each wire 19 is then turned around the outer face of the polyurethane tube 11 for at least one turn to thereby form one electrode of a series of electrodes 23.

The catheter 10 comprises a series of longitudinally spaced apart small holes each extending from the inner face of the lumen 13 to the outer face of the polyurethane tube 11. The non-isolated free end sections of the wires 19 are passed through the respective, longitudinally spaced apart holes extending from the inner face of the lumen 13 to the outer face of the polyurethane tube 11, and the exposed non-isolated free end sections of the wires 19 are turned around the outer face of the tube 11 for at least one turn to form the series of longitudinally spaced apart electrodes 23. As illustrated in FIG. 3, the longitudinal spacing between every pair of mutually adjacent electrodes 23 may be constant (constant inter-electrode distance).

The series of electrodes 23 may comprise a ground/reference electrode.

The electrical wires 19 can be made of stainless steel coated with Teflon; however, other wire materials such as silver, gold, copper, etc. can be used. As well, wire isolation can be made of any other suitable electrically isolating material.

In an alternative electrode design, a plurality of wires (isolated or non isolated) 19 can run through separate lumens of the catheter 10. Again, the electrodes 23 would be obtained by exposing each bared end section of the electrical wires through a hole in the wall of the polyurethane tube 11. The wires 19 will still be electrically and individually isolated between the electrodes 23 and the first amplifier stage (not shown).

Gastric 24 and esophageal 25 inflatable balloons are longitudinally spaced apart on the catheter 10 and positioned on respective opposite sides of the series of electrodes 23. The balloons 24 and 25 are made of medical grade polyurethane and are mounted and fixed to the catheter 10 through hydrophilic medical grade polyurethane commercialized under the trademark Hydromed D3.

Holes such as 26 extend from the inside of the pressure lumen 15 to the inside of the gastric balloon 24 to enable inflation and deflation of this gastric balloon 24 through the pressure lumen 15 and the pressure connector 17. In the same manner, holes such as 27 extend from the inside of the pressure lumen 14 to the inside of the esophageal balloon 25 to enable inflation and deflation of this esophageal balloon 25 through the pressure lumen 14 and the pressure connector 18. In operation, the gastric 24 and esophageal 25 balloons are deflated to insert and remove the esophageal catheter 10. After insertion of the catheter, the gastric 24 and esophageal 25 balloons are inflated to fixedly position the series of electrodes 23 with respect, for example, the subject's diaphragm in order to take measurements of the EMG activity of the subject's diaphragm.

Finally, a series of longitudinally spaced apart holes such as 28 extend from the inner face of the larger-diameter lumen 12 to the outer face of the polyurethane tube 11 between the gastric balloon 24 and the free end 29 of the catheter 10. Holes 28 will enable feeding of the subject through the connector 21 (FIG. 2), the larger-diameter lumen 12 (FIG. 1) and the series of longitudinally spaced apart holes 28 (FIG. 3).

Coating

The inter-electrode conductive medium can be formed of a conductive material such as a semi-conductor, an absorbent material, a carbonized material, a liquid-containing material, an electrolyte, etc. The choice of the conductive material depends in part on whether the electrodes 23 will be subjected to a wet or dry environment. For example, whereas hydrophilic and absorbent materials are suitable for wet environments, hydrogels are more suitable for dry environment. Semi-conductor polymers and carbonized, or in other way made conductive materials can be used in both environments.

In the present illustrative embodiment, the outer face of the polyurethane tube 11 of the catheter 10 as well as the electrodes 23 are first coated with a first layer of hydrophilic medical grade polyurethane (HydroMed™ D3, 50% water content) to fix the electrodes 23 on the outer face of the polyurethane tube 11. A second layer of hydrophilic medical grade polyurethane (HydroMed™ 640, 90% water content) is applied to the first layer of HydroMed™ D3 to provide a slippery lubricious interface to surrounding tissue. The photograph of FIG. 4 illustrates an electrode 23 embedded in this double coating, forming the above mentioned inter-electrode conductive medium having a given resistivity for controlling resistivity between the electrodes 23 of the series.

Those of ordinary skill in the art will understand that the coating of the outer face of the polyurethane tube 11 and the electrodes 23 can be a single-layer coating or a multi-layer coating made of any suitable medical grade material other than HydroMed™ D3 (50% water content) and HydroMed™ 640 (90% water content).

Moreover, the above-mentioned ground/reference electrode can be one of the electrodes 23, it can be integrated into the inter-electrode conductive medium or, more simply, even be formed by this inter-electrode conductive medium.

FIG. 5 depicts signals obtained from an electrode array using a reference amplifier and digital differentiation for, on the left side, the previous technology (old technology) and for, on the right side, the technology according to the present invention (new technology).

In FIG. 5, the series of electrodes 23 is surrounded by tissue nearby the subject's diaphragm. According to the previous technology (old technology), when the electrodes 2–8 (forming part of the series of electrodes 23) are covered with no inter-electrode conductive medium, both channel Ch4 (electrodes 4 and 5) and channel Ch5 (electrodes 5 and 6) must be turned off when subjected to unmanageable DC offset. With the technology of the present invention (new technology), the electrodes 4, 5 and 6 are covered by the inter-electrode conductive medium (indicated by the gray area); in this manner DC offsets are avoided and signals are maintained along all channels of the electrode array.

Operation of the Illustrative Embodiment of the Electrode Array

In the illustrative embodiment of the electrode array:
the electrodes of the series are made of a material having a first resistivity;
the biological tissue has a second resistivity;
the inter-electrode conductive medium is made of a material having a third resistivity considerably higher than the first resistivity; this third resistivity is located within a range near the second resistivity of the subject's biological tissue. Since the inter-electrode conductive medium should not act as a short-circuit, the third resistivity will not be too low compared with the second resistivity of the subject's biological tissue; the third resistivity can even be slightly higher than the second resistivity.

When an electrode loses contact with the patient's tissue, the transmitted disturbance comes from a high-impedance source. A reasonable conductance between the electrodes 23 can neutralize this disturbance. When the contact between one or more electrode(s) 23 and the subject's tissue is poor, but at least one electrode 23 (and the reference/ground electrode, if it is not coated with the inter-electrode conductive medium) presents a good contact with subject's tissue, the inter-electrode conductive medium still provides, by controlling the resistivity between the electrodes 23, a defined signal potential on the electrode(s) having lost contact, which represents a mean value of signal potentials on the neighbouring electrodes, whereas capacitive and/or inductive disturbances are controlled.

In other words, in operation, when contact between at least one of the electrodes 23 of the series and a subject's biological tissue is poor, the inter-electrode conductive medium forms a means for producing on this at least one electrode an estimate of the electrical activity in the biological tissue, this estimate being constituted by a mean value of electrical potentials produced on neighbouring electrodes 23 of the series by the electrical activity in the subject's biological tissue.

In this manner, voltage between electrodes that have maintained contact with the subject's biological tissue and those that have lost connection with this biological tissue is minimally altered.

Advantages

The illustrative embodiment of the electrode array according to the present invention presents, amongst others, the following advantages:
the electrode array limits disturbances when contact is lost between one or more electrodes and the subject's tissue;
it prevents electrodes having no or poor contact with the patient's tissue from inducing signal disturbances and instead replaces the disturbance with an estimate of the signal activity in the region/area of concern;
it makes it possible to measure down to very low signal frequencies;
it prevents loss of reference/ground since the inter-electrode conductive medium extends over the entire series of electrodes including the reference/ground electrode;
it minimizes disturbances of inductive or other nature by creating a stabilizing interface environment;
the coating (inter-electrode conductive medium) encapsulates edges and protruding parts to reduce risk of tissue irritation and/or damage. Slippery coating materials such as hydrophilic polymers and hydrogels reduces friction with tissue, and facilitates placement of the electrode array through, for example, the esophagus; and
it makes it possible to increase the gain in a first differential amplifier stage.

Although the present invention has been described in the foregoing specification by means of a non-restrictive illustrative embodiment, this illustrative embodiment can be modified as will, within the scope of the appended claims without departing from the nature and spirit of the subject invention.

What is claimed is:

1. An electrode array, comprising:
an electrode support;
a group of electrodes mounted on the electrode support for measuring electrical activity in a subject's biological tissue; and
an inter-electrode conductive medium having a given resistivity for controlling, during electrical activity measurement, resistivity between the electrodes of the group to improve said electrical activity measurement, the inter-electrode conductive medium including a coating formed of a first layer of conductive material applied to at least one electrode of the group and to the electrode support between the electrodes and a second layer of slippery conductive material applied to the first layer of conductive material to provide a lubricious interface to the subject's biological tissue, wherein, when electrical contact between at least one electrode of the group and the subject's biological tissue is poor, the inter-electrode conductive medium forms a means for producing on said at least one electrode an estimate of the electrical activity in the subject's biological tissue, said estimate being a mean value of electrical potentials produced on neighbouring electrodes of the group by the electrical activity in the subject's biological tissue.

2. An electrode array as defined in claim 1, wherein the inter-electrode conductive medium includes a reference electrode.

3. An electrode array as defined in claim 1, wherein:
the electrodes of the group are made of a material having a first resistivity; and
the inter-electrode conductive medium has a second resistivity considerably higher than the first resistivity.

4. An electrode array as defined in claim 1, wherein:
the subject's biological tissue has a first resistivity; and
the inter-electrode conductive medium has a second resistivity situated within a range near the first resistivity.

5. An electrode array as defined in claim 1, wherein the conductive material of at least one of the first and second layers of the coating is selected from the group consisting of: a semi-conductor, a semi-conductor polymer, an absorbent material, a hydrophilic material, a carbonized material, a liquid containing material, an electrolyte, and a hydrogel.

6. An electrode array as defined in claim 1, wherein the electrode array is a linear array of electrodes.

7. An electrode array as defined in claim 1, wherein the electrically conductive material of the first layer of the coating includes hydrophilic medical grade polyurethane.

8. An electrode array as defined in claim 7, wherein the hydrophilic medical grade polyurethane has a water content of about 50%.

9. An electrode array as defined in claim 1, wherein the electrically conductive material of the second layer of the coating includes hydrophilic medical grade polyurethane.

10. An electrode array as defined in claim 9, wherein the hydrophilic medical grade polyurethane has a water content of about 90%.

11. An electrode array, comprising:
a catheter with a distal end section;
a series of electrodes mounted on the distal end section of the catheter for measuring electrical activity in a subject's biological tissue; and
an inter-electrode conductive medium having a given resistivity for controlling, during electrical activity measurement, resistivity between the electrodes of the series to improve said electrical activity measurement, the inter-electrode conductive medium including a coating formed of a first layer of conductive material applied to at least one electrode of the series and to the catheter between the electrodes and a second layer of slippery conductive material applied to the first layer of conductive material to provide a lubricious interface to the subject's biological tissue,
wherein, when contact between at least one electrode of the series and the subject's biological tissue is poor, the inter-electrode conductive medium forms a means for producing on said at least one electrode an estimate of the electrical activity in the subject's biological tissue, said estimate being a mean value of electrical potentials produced on neighbouring electrodes of the series by the electrical activity in the subject's biological tissue.

12. An electrode array as defined in claim 11, wherein the inter-electrode conductive medium includes a reference electrode.

13. An electrode array as defined in claim 11, wherein:
the electrodes of the series are made of a material having a first resistivity; and
the inter-electrode conductive medium has a second resistivity considerably higher than the first resistivity.

14. An electrode array as defined in claim 11, wherein:
the subject's biological tissue has a first resistivity; and
the inter-electrode conductive medium has a second resistivity situated within a range near the first resistivity.

15. An electrode array as defined in claim 11, wherein the conductive material of at least one of the first and second layers of the coating is selected from the group consisting of: a semi-conductor, a semi-conductor polymer, an absorbent material, a hydrophilic material, a carbonized material, a liquid containing material, an electrolyte, and a hydrogel.

16. An electrode array as defined in claim 11, wherein the series of electrodes have a constant inter-electrode distance.

17. An electrode array as defined in claim 11, wherein:
the catheter comprises an outer face and a lumen through which isolated electrical wires run;
the electrical wires comprise respective non isolated distal end sections;
the distal end section of the catheter comprise a series of holes extending from the lumen to the outer face of the catheter; and
the non isolated distal end section of each electrical wire extends through a corresponding one of said holes and is turned around the outer face of the catheter for at least one turn to form one of the electrodes of the series.

18. An electrode array as defined in claim 11, further comprising two pressure balloons mounted on the catheter on respective opposite sides of the series of electrodes, wherein the catheter comprises pressure lumens through which the pressure balloons are inflated to fixedly position the series of electrodes about the subject's biological tissue.

19. An electrode array as defined in claim 11, wherein:
the catheter comprises an outer face and a plurality of lumens;
the electrode array comprises a plurality of electrical wires running through the lumens of the catheter, respectively; and
each electrical wire comprises a non insulated distal end section exposed on the outer face of the catheter to form one of the electrodes of the series, the non insulated distal end section of said electrical wire being exposed through a hole extending from the corresponding lumen to the outer face of the catheter.

20. An electrode array as defined in claim 11, wherein the electrically conductive material of the first layer of the coating includes hydrophilic medical grade polyurethane.

21. An electrode array as defined in claim 20, wherein the hydrophilic medical grade polyurethane has a water content of about 50%.

22. An electrode array as defined in claim 11, wherein the electrically conductive material of the second layer of the coating includes hydrophilic medical grade polyurethane.

23. An electrode array as defined in claim 22, wherein the hydrophilic medical grade polyurethane has a water content of about 90%.

24. An electrode array, comprising:
a catheter with a distal end section;
a series of electrodes mounted on the distal end section of the catheter; and an inter-electrode conductive medium having a given resistivity for controlling resistivity between the electrodes of the series, wherein the inter-electrode conductive medium comprises a coating formed of:
a first layer of hydrophilic medical grade polyurethane applied to both the electrodes of the series and an outer face of the catheter between the electrodes; and
a second layer made of a slippery material and applied to the first layer to form a lubricious interface to the subject's biological tissue.

25. A method of controlling an inter-electrode resistivity in an electrode array including a group of electrodes for measuring electrical activity in a subject's biological tissue, comprising applying an inter-electrode conductive medium having a given resistivity between the electrodes of the group, the inter-electrode conductive medium including a coating formed of a first layer of conductive material applied to the electrodes of the group and a second layer of slippery conductive material applied to the first layer of conductive material to provide a lubricious interface to the subject's biological tissue, and interconnecting the electrodes of the group through said inter-electrode conductive medium to thereby control, during electrical activity measurement, resistivity between said electrodes to improve said electrical activity measurement, said method further comprising, when contact between at least one electrode of the group and the subject's biological tissue is poor, producing on said at least one electrode an estimate of the electrical activity in the subject's biological tissue through the inter-electrode conductive medium, said estimate being a mean value of electrical potentials produced on neighbouring electrodes of the group by the electrical activity in the subject's biological tissue.

26. A method as recited in claim 25, further comprising including a reference electrode to the inter-electrode conductive medium.

27. A method as recited in claim 25, wherein:
the electrodes of the group are made of a material having a first resistivity; and
said method comprises providing an inter-electrode conductive medium having a second resistivity considerably higher than the first resistivity.

28. A method as recited in claim 25, wherein:
the subject's biological tissue has a first resistivity; and
said method comprises providing an inter-electrode conductive medium having a second resistivity situated with a range near the first resistivity.

29. A method as recited in claim 25, wherein:
the electrode array comprises a support for the electrodes; and
interconnecting the electrodes of the group through the inter-electrode conductive medium comprises applying the first layer of the coating of said electrically conductive medium on the electrodes of the group and the electrode support between the electrodes.

30. A method as recited in claim 29, wherein applying the first layer of the coating comprises applying a material selected from the group consisting of: a semi-conductor, a semi-conductor polymer, an absorbent material, a hydrophilic material, a carbonized material, a liquid containing material, an electrolyte, and a hydrogel.

* * * * *